(12) United States Patent
Irazoqui-Pastor et al.

(10) Patent No.: US 7,346,312 B2
(45) Date of Patent: Mar. 18, 2008

(54) WIRELESS NEURAL DATA ACQUISITION SYSTEM

(75) Inventors: Pedro Irazoqui-Pastor, Durham, NC (US); James C Morizio, Durham, NC (US); Vinson L Go, Wake Forest, NC (US); Jack D Parmentier, Apex, NC (US)

(73) Assignee: Triangle BioSystems, Inc., Durham, NC (US)

( * ) Notice: Subject to any disclaimer, the term of this patent is extended or adjusted under 35 U.S.C. 154(b) by 320 days.

(21) Appl. No.: 10/971,915

(22) Filed: Oct. 23, 2004

(65) Prior Publication Data

US 2006/0089112 A1 Apr. 27, 2006

(51) Int. Cl.
*H04B 1/04* (2006.01)
*A61B 5/04* (2006.01)

(52) U.S. Cl. ............... 455/41.2; 455/334; 455/349; 600/546; 600/373

(58) Field of Classification Search ............ 455/232.1, 455/296, 307, 311, 313, 334, 341, 344, 41.2, 455/42, 349; 600/546, 373, 300; 330/278, 330/295
See application file for complete search history.

(56) References Cited

U.S. PATENT DOCUMENTS 6,402,689 B1 * 6/2002 Scarantino et al. ......... 600/300

7,187,967 B2 * 3/2007 Kennedy ................... 600/544
2005/0090756 A1 * 4/2005 Wolf et al. ................. 600/546

OTHER PUBLICATIONS

Pedram Mohseni, Khalil Najafi, "A Low Power Fully Integrated Bandpass Operational Amplifier for Biomedical Neural Recording Applications," 24th Annual International Conference of the IEEE Engineering in Medicine and Biology Society, Houston, TX (Oct. 23-26, 2002).
Pedro Irazoqui-Pastor, Istvan Mody, and Jack W. Judy, "In-Vivo EEG Recording Using a Wireless Implantable Neural Transceiver," 1st International IEEE EMBS Conference on Neural Engineering, Capri Island, Italy (Mar. 20-22, 2003).
Irazoqui-Pastor, Pedro. (2003) Transcutaneous Inductively Powered Neural Recording System [Doctoral Dissertation].University of California: Los Angeles (CA).

* cited by examiner

*Primary Examiner*—Blane J. Jackson
(74) *Attorney, Agent, or Firm*—MacCord Mason PLLC (57) ABSTRACT

A Wireless Neural Data Acquisition System for increased power efficiency, compact size, robust signaling and reliable transmission is shown and described. In one embodiment, the system includes a headstage, an RF receiver, an analog-to-digital converter, a digital signal processor, and a communication interface. The headstage includes at least one input pre-amplifier high-pass filter and amplifier, a multiplexer (MUX), an RF Modulator comprising a voltage control oscillator (VCO), a transmitting antenna, and a power supply. The RF receiver includes at least one receiving antenna, at least one bandpass filter, at least one amplifier, at least one attenuator, and an FM Demodulator.

55 Claims, 5 Drawing Sheets

WIRELESS NEURAL DATA ACQUISITION SYSTEM

BACKGROUND OF THE INVENTION (1) Field of the Invention

The present invention relates generally to neural monitoring and, more particularly, to wireless neural data acquisition.

(2) Description of the Prior Art

The use of wireless devices to capture neural data is known in the art. Irazoqui-Pastor et al. in *"In-Vivo EEG Recording Using a Wireless Implantable Neural Transceiver,"* 1st International IEEE EMBS Conference on Neural Engineering, Capri Island, Italy (Mar. 20-22, 2003) describe recording in-vivo EEG signals using a wireless implantable neural transceiver. This device is inductively powered, does not have selectable gain, digital programmability, or band-pass capability. This device also uses differential input amplifiers, does not use a multiplexer (MUX) and thus it can only record from a single channel. It uses an inefficient voltage-control oscillator (VCO) with a power amplifier, which provides low transmission range and low reliability with large power consumption. This invention also uses a cumbersome and unreliable monopole antenna. Furthermore, this invention does not have a receiver.

Pedram Mohseni and Khalil Najafi in *"A Low Power Fully Integrated Bandpass Operational Amplifier for Biomedical Neural Recording Applications,"* 24th Annual International Conference of the IEEE Engineering in Medicine and Biology Society, Houston, Tex. (Oct. 23-26, 2002) teach a system that uses a single sub-threshold metal oxide semiconductor field-effect transistor (MOSFET) at the input to adjust the RC pole location generated by the capacitance between the recording electrode and the biological tissue. The device was tuned using on-chip resistors which had to be laser-trimmed individually for each chip, which then worked only with the electrode for which it had been trimmed. Additionally the amplifiers experienced significant drift as a result of the manner in which the input was connected.

These prior art inventions have either poor reliability and/or are impractical for large-scale use. Thus, a need exists for a wireless multi-channel neural data acquisition system that is of robust design, low power-consumption, and flexible with tunable bandpass filtering and selectable gain.

SUMMARY OF THE INVENTION

The present invention is directed to a wireless neural data acquisition system for monitoring neural activity.

The present invention is further directed to a wireless neural data acquisition headstage.

The present invention is still further directed to a device for amplifying a signal.

The present invention is alternatively further directed to a method of using a wireless neural data acquisition system for monitoring.

Accordingly, one aspect of the present invention is to provide a wireless neural data acquisition system, including: a headstage, an RF receiver, an analog-to-digital converter, a digital signal processor, and a communication interface. The headstage comprising: at least one Input Pre-amplifier high-pass filter and amplifier, a multiplexer (MUX), an RF Modulator comprising a voltage control oscillator (VCO), a transmitting antenna, and a power supply. The RF receiver comprising: at least one receiving antenna, at least one RF bandpass filter, at least one RF amplifier, at least one RF attenuator, and an FM Demodulator. The pre-amplifier is a dual on-chip sub-threshold MOSFETs for each channel with two off-chip tuning resistors for all channels, the impedance of the RF modulator is such that it allows the MUX to drive the RF stage directly, the antenna impedance is matched to the VCO output, the FM demodulator is an FM phase discriminator, and the A/D converter and DSP provide real-time signal processing. The components are connected such that the input signal coming from the electrode goes through a high-pass filter then to the amplifier then to the MUX then to the RF modulator then to the transmitting antenna then to the RF receiver antenna(s) then to at least one bandpass filter, amplifier, and attenuator then to the FM demodulator then to the communication interface. Thus providing increased power efficiency, compact headstage size, robust wireless signaling, and multiplexing for accurate, reliable transmission of neural signal data.

Another aspect of the present invention is to provide a wireless neural data acquisition headstage, comprising:
  at least one Input Pre-amplifier band-pass filter and amplifier,
  a multiplexer (MUX)
  an RF Modulator comprising a voltage control oscillator (VCO)
  a transmitting antenna
  and a power supply.
  wherein the pre-amplifier is a dual on-chip sub-threshold MOSFETs for each channel with two off-chip tuning resistors for all channels, the impedance of the RF modulator is such that it allows the MUX to drive the RF stage directly, and the antenna impedance is matched to the VCO output;
  wherein the components are connected such that the input signal coming from the electrode goes through a bandpass filter then to the amplifier then to the MUX then to the RF modulator then to the transmitting antenna;
  thereby providing
  increased power efficiency, compact headstage size, robust wireless signaling and multiplexing for accurate, reliable transmission of neural signal data.

Yet another aspect of the present invention is to provide a device for amplifying a signal, comprising: at least one Input Pre-amplifier band-pass filter and amplifier; wherein the pre-amplifier is a dual on-chip sub-threshold MOSFETs for each channel with two off-chip tuning resistors for all channels.

Still another aspect of the present invention is to provide a method of neural data monitoring, comprising the steps of: A. providing a wireless neural data acquisition system according to the present invention and B. acquiring data from the wireless neural data acquisition system.

These and other aspects of the present invention will become apparent to those skilled in the art after a reading of the following description of the preferred embodiment when considered with the drawings.

DETAILED DESCRIPTION OF THE PREFERRED EMBODIMENTS

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto.

Wireless Neural Data Acquisition System

Figure 1:
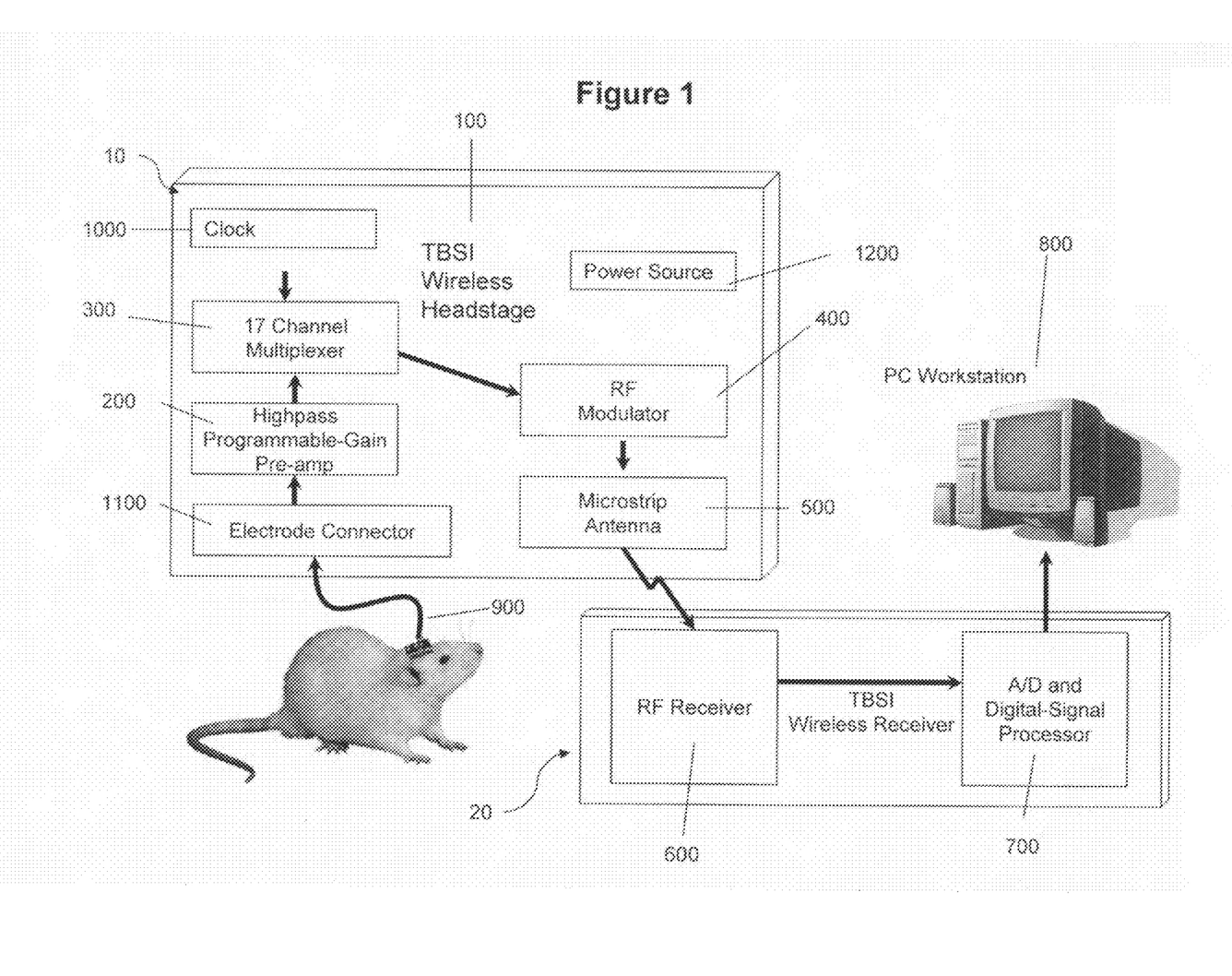
FIG. 1 is a schematic diagram of a system constructed according to the present invention.

The wireless neural data acquisition system according to the present invention, generally described as 10 in FIG. 1, includes a transmitter or headstage 100, an RF receiver 600, an analog-to-digital (A/D) converter and digital signal processor (DSP) 700, and an output device 800.

Headstage

The headstage 100 is a packaged device that is secured on an animal's skull and is connected via electrode connector 1100 to implanted electrodes 900. The headstages may also be encapsulated in commercially available biocompatible epoxies to allow them to be chronically implanted in test subjects if the user wishes to do so.

The headstage receives neural activity data from the electrodes 900, then amplifies, filters, and transmits the neural activity data to a receiver 600. The headstage includes an electrode connector 1100, a pre-amp 200 for each input channel, a multiplexer (MUX) 300, an RF modulator 400, an input control 180, which preferably includes a clock, an antenna 500, and a power supply 1200.

Figure 2:
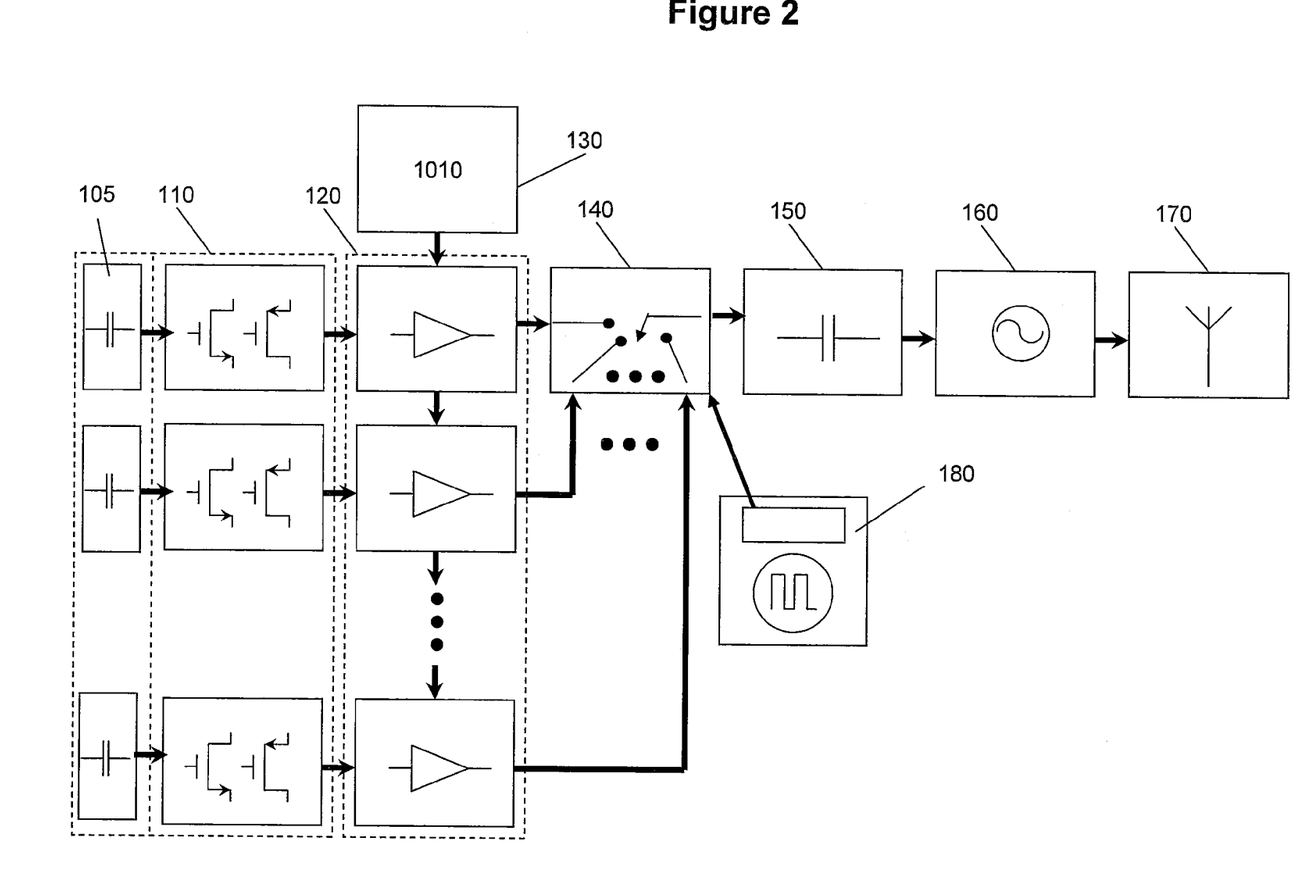
FIG. 2 is a schematic diagram of a wireless transmitter according to the present invention.

The head stage, shown schematically in FIG. 2, includes several components. Any type and combinations of neural electrodes can be used as the signal input electrode. The inputs from an electrode array are high passed filtered by a series coupling capacitor along with two sub-threshold MOSFETs per channel in 110, before being sent on to a low-noise, low-power preamp 120. The gain of each preamp is individually selectable via the digital logic 130 which receives its input from off-chip jumpers. Once filtered and amplified, neural signals are time-division multiplexed (TDM) in the multiplexer (MUX) 140. The sequencing of the MUX analog switches is controlled, at least in part, by input control 180, which preferably includes a clock. The output of which is ac-coupled 150 into a radio-frequency (RF) voltage-controlled oscillator (VCO) 160. The oscillator output is a frequency modulated (FM) representation of the MUX output, and drives an impedance-matched miniaturized planar-microstrip antenna 170.

Input/Pre-amps

Figure 3:
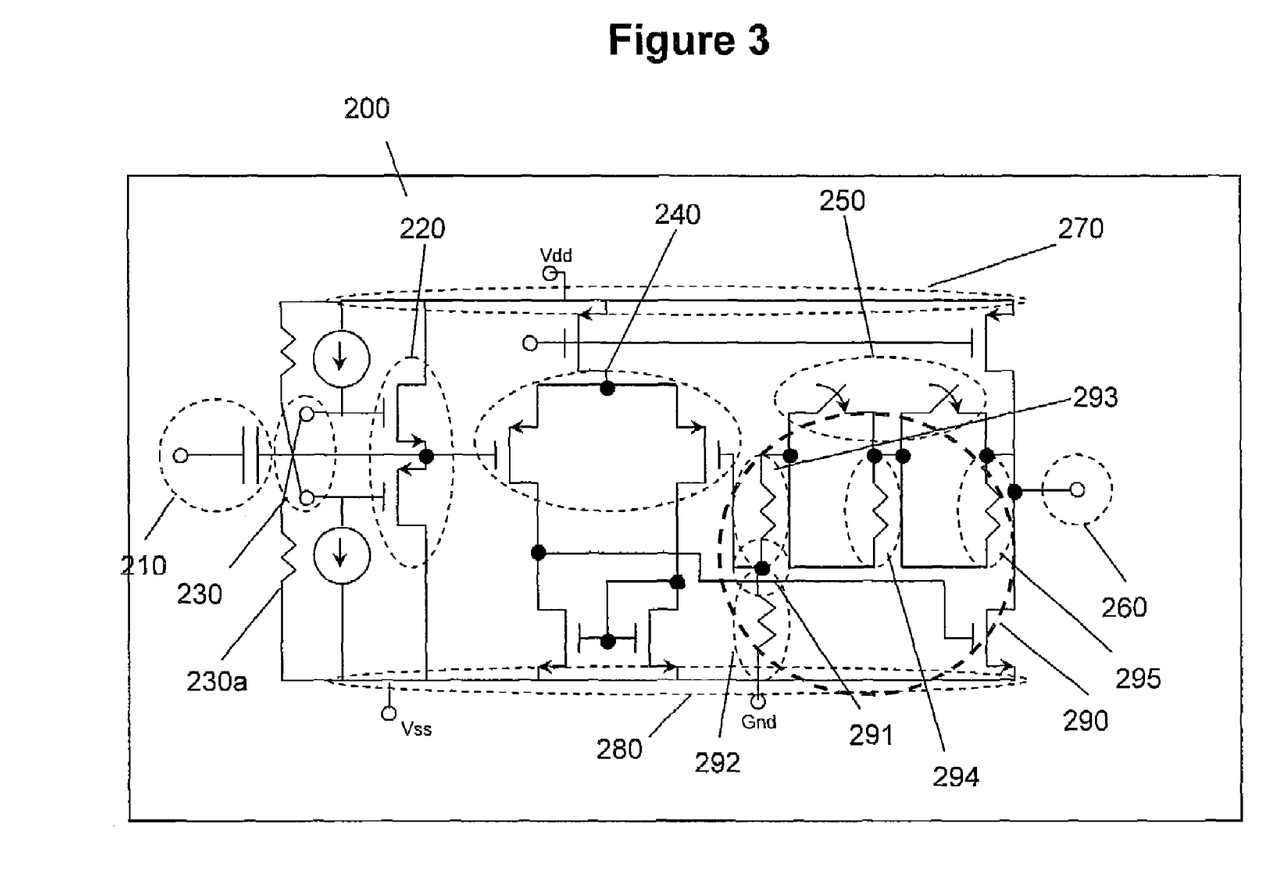
FIG. 3 is a schematic diagram of a subthreshold MOSFET preamp according to the present invention.

The input pre-amplifier 200, as shown in FIG. 3, is the front-end of the entire system. It records the signal of interest directly from the brain of the implanted subject, and is thus the most critical in terms of noise and distortion contributions to the overall system. Because the signal amplitude is greater as it exits the pre-amp, constant-amplitude white-noise sources that are critical in this stage, become far less important in subsequent stages. Beyond preserving the purity of the recorded signal, the front-end must amplify the signal before passing it on to subsequent stages, and filter out any out-of-band signals. There are a broad range of parameters: gain, output swing, linearity, and bandwidth, as well as noise tolerances which have been specified and designed into the final amplifier. Since it is not possible to optimize all of these parameters, trade-offs must be made which are dependent on the application. This is one reason why off-the-shelf solutions do not work, and a custom integrated circuit (IC) was designed and fabricated for the present invention to address problems of the existing solution.

Neural signals can range from 2-Hz for EEGs up to 10 kHz for single unit action potentials. The amplifier design uses an innovative solution to high-pass filter the input with a user-selectable cutoff frequency. Additionally the gain-bandwidth product of the amplifier is adjusted to low-pass filter input signals above 10 kHz since no biological signals are present above this point. High-pass filtering in the amplifier is achieved by capacitively coupling 210 the input signal from the recording electrode to the amplifier input, and using a pair of MOSFET devices 220 operating in the sub-threshold region to set the RC pole. These two devices are connected between the non-inverting amplifier input-node 291 and the positive and negative power rails 270 and 280, respectively. Battery/power connection Vdd connects to power rail 270 and connections Vss and GND connect to power rail 280. Using a single off-chip resistor 230a connected at terminal 230, the gate voltage of each input MOSFET can be adjusted, thereby regulating the effective resistance presented by the MOSFETs at the input node and thereby set the high-pass cutoff frequency. This can be decreased for measuring EEGs, or increased to block out EEGs when single-neuron activity is of interest. MOSFETs are used because they provide high impedance for a given amount of chip area, greatly reducing manufacturing costs. Using two devices going to opposite power rails allows the input offset voltage to the amplifier to be adjusted to overcome the small imbalance in the differential-pair 240 present in any complimentary metal-oxide semiconductor (CMOS) manufacturing process and eliminate the amplifier output offset. This configuration also eliminates the possibility of output signal drift over time seen in some single MOSFET implementations. The small input coupling capacitor 210 is also located on chip to reduce the size of the headstage. This capacitor is typically much smaller than that present at the electrode-tissue interface, making it the dominant one in a series connection. Thus, while the capability remains to optimize the sub-threshold device impedances using the off-chip resistors with the particular recording electrodes being used, using the present topology makes it generally unnecessary to do so.

Another key parameter of the pre-amp according to the present invention is gain, which is intimately related to the output swing, linearity, and power consumption of the amplifier. Gain is a function of the topology chosen and the power available. For any given topology, the higher the power consumption, the greater the gain. Neural signals range in amplitude from microvolts to tens of millivolts, and can be classified into three broad categories—small, single neuron input signals, mid-range large-amplitude single-neuron action potentials from cells adjacent to the recording electrodes and small EEG signals arising from distant neuron populations, and much larger EEG signals. Working backwards from the output VCO, it is known that the maximum input range of that RF stage is 500 mV peak-to-peak. Moreover, concentrating all of the system gain into the input stage maximizes the overall signal-to-noise ratio. This means that if there is a very small single-neuron input signal of 10-100 µV, an ideal gain would be on the order of 5000, whereas for a much larger EEG signal of 1-10 mV, the maximum gain would be on the order of 50. In between the small single-neuron input signals and EEG signals lie large-amplitude single-neuron action potentials from cells adjacent to the recording electrodes and small EEG signals arising from distant neuron populations. These range in amplitude from 100 µV to 1 mV and constitute a small majority of the data recorded in a typical neurophysiologic setup. In order to maximize the present invention's range without overdriving the MUX and in turn the VCO, these signals would optimally have a gain within an order-of-magnitude of 500. When an array of recording electrodes is inserted into the brain, a number of electrodes will fall into each of the three broad categories. One of the major innovations of the preamp according to the present invention is that it provides selectable gain either for all the channels in the headstage simultaneously as explained below, or for each channel individually through off-chip jumpers. This allows an unprecedented amount of flexibility in neural recording. Upon powering up the system, the user can observe the types of signals present at each channel and tailor the gain of that channel individually. This increases the amount of data being effectively processed by the input stage, and greatly reduces the need for multiple insertions of the electrode arrays to obtain a higher signal yield on all channels, something which is very damaging to the neural tissue being examined.

The variable gain is achieved by first configuring a differential two-stage operational amplifier in a standard non-inverting resistor feedback configuration, generally shown as 295 in FIG. 3. Then, the ratio of the feedback resistors is adjusted to give a highest gain. The larger of the two resistors 293-295 is then divided into three parts, of which the first part 293 is 50 times larger than the smaller resistor 292, the second part 294 is 9 times greater than the first, and the third part 295 is 9 times greater than the second. By then connecting MOS switches 250 to either end of the second 294 and third parts 295 they are switched in and out of the feedback circuit. In this manner the gain at the output 260 can be adjusted in discreet increments of 50, 500 and 5000. The specific values are chosen in order to work well with the rest of this system. In a different application the same gain-control mechanism could yield any combination of discreet gain values desired. By connecting the on/off terminal of the switches for each input preamp to a digital logic block 130, shown in FIG. 2, integrated with the IC, the user can then scan in the desired gain for each amplifier and then store it in on-chip memory, varying these as needed over the life-cycle of the device.

Multiplexer (MUX)

Figure 4:
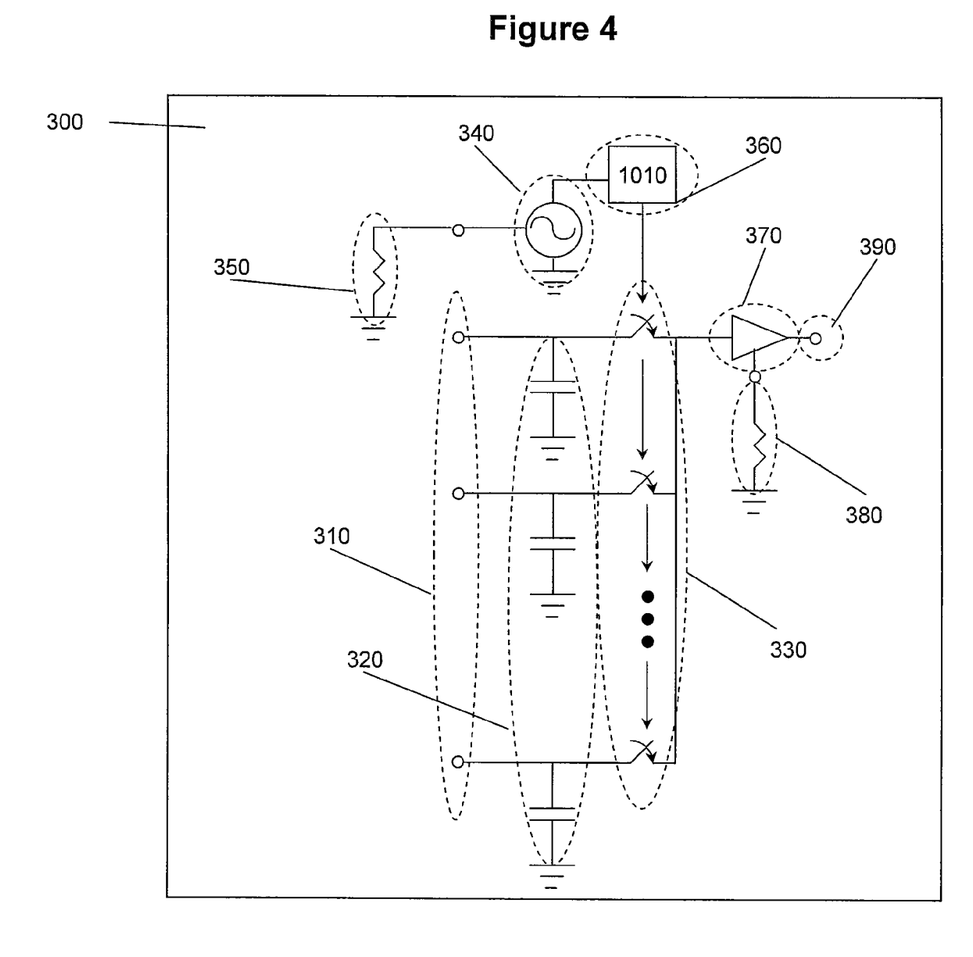
FIG. 4 is a schematic diagram of a multiplexer according to the present invention.

The MUX 300, shown in more detail in FIG. 4, receives the signals from the pre-amps and converts them into a single channel using time-division multiplexing (TDM). The MUX takes the input channel signals; time slices them, and then merges them into a single signal for output to the RF modulator.

The MUX provides rapid signal settling through properly tuned charge injection in order to increase the number of channels that can be multiplexed. The sampling rate limit is a function of the MUX output settling time and the speed of the internal clock which can be controlled through an off-chip resistor. The MUX output settles quickly enough so that a clean sample can be taken before the MUX switches to the next channel. Alternatively, the sampling rate can be slow enough such that the MUX output signal has settled sufficiently so that an accurate sample can be taken before the MUX switches to the next channel.

Any number of channels may be multiplexed, provided that the frequency of the clock at least equals the product of the number of channels and the desired sampling rate per channel. In the MUX according to the present invention, the sampling rate can go up to 5 MHz allowing 100 channels at the industry standard 50 kHz sampling-rate per channel for neural signals, or 250 channels at the minimum 20 kHz per channel for biological signals, which are band-limited to 10 kHz. In the prototype headstage the number of channels multiplexed is 17, composed of 16 data input channels and 1 reference channel driving the MUX input nodes 310. These then charge the MOS storage capacitors 320. A ring oscillator 340 generates a clock signal at a frequency determined by an off-chip tuning resistor 350. The clock signal drives a digital logic block 360 which cyclically rotates through the array of switches 330 determining which single channel drives the output buffer amplifier 370 at any given time. The slew-rate, and current-driving capabilities of the output buffer, can also be adjusted by an off-chip resistor 380. The buffered TDM output is then presented to the MUX output 390 which drives the RF modulator.

When the MUX according to the present invention is run at 850 kHz, well below its capacity and thus at lower power, this frequency results in each channel being sampled at 50 kHz. In a preferred embodiment of the present invention, 16 data channels are adequate for most neurological applications, however, the present invention can be designed to multiplex at least about 32 channels, and an increased number of channels multiplexed is contemplated as applications requiring the use of more channels are developed.

The present invention's multiplexer is a low power consumption design. Low power-consumption is achieved through the use of a carefully tuned current-starved ring oscillator 340, and low-power output-buffer 370. This is possible because the MUX only needs enough power to drive the capacitive load presented by the VCO, not the 50 Ω load required for most off-the-shelf multiplexers designed for other types of applications. The low power consumption MUX according to the present invention draws less than about 3 mA from a 2.8 V supply for a total power consumption less than about 9 mW, permitting longer operation periods of the system.

The RF modulator 400 is a high-frequency, wide-band Voltage Controlled Oscillator (VCO). The carrier wave frequency is designed for the microwave spectrum to reduce antenna size, but on the lower end of the microwave spectrum so as to not be impeded by biological tissue. Thus, the frequency used can range from between about 2.4 GHz to no greater than about 4 GHz. At the bottom end of this range, 2.4 GHz, water molecules resonate, effectively blocking signal propagation. Additionally there is a large amount of third-party interferers from local 802.11 WiFi and Bluetooth networks. At the high end of this range, signal attenuation through the biological milieu becomes excessive. The present invention includes three VCOs designed with a center frequency of 2.8, 3.2, and 3.6 GHz.

The RF modulator 400 uses wideband frequency modulation, modulating the frequency to about 10% of center frequency. For example, a 3.2 GHz center frequency is modulated about a 300 MHz band. Thus, the frequency band is between about 3.05 to about 3.35 GHz for one transmitter. Other transmitters with 300 MHz bandwidths centered at 2.8 GHz and 3.6 GHz have been built. These 3 center frequencies can be used with a 300 MHz bandwidth simultaneously without overlap. This use of frequency diversity permits the operation of multiple devices in the same area simultaneously.

Advantageously, the wideband frequency modulation reduces the sensitivity to phase noise, thereby obviating some of the more complex, power-intensive, and unreliable techniques commonly used to reduce phase noise in CMOS cross-coupled VCOs.

The antenna 500 is preferably a microstrip patch antenna. Both rectangular and planar inverted-f (PIFA) patch antennas are used in our system. A microstrip patch antenna is advantageous in several respects. It has a planar form that is easy to integrate into the headstage and biological systems in general; its signal pattern is more reliable than other antenna designs; and power consumption is reduced with respect to other types of antennas. Additionally, microstrip patch antennas are mass produced more economically than other antenna designs and can be integrated onto the headstage circuit board.

Alternative antenna designs include monopole, dipole, and whip antennas. Of these, the monopole is the most desirable, as they all perform similarly, but the monopole is the smallest. The advantage of the patch over the monopole lies in the improved radiation pattern, and better form factor.

Antennas designed to operate in free-space have their maximum radiating dimension, and thus their overall size, determined by the wavelength of the transmit signal frequency and the relative permittivity, which is 1 in free-space. Implanting microstrip antennas in biological tissues places them in an environment with a relative permittivity on the order of 35 for skin, allowing them to be substantially reduced in overall size and thus the overall size of the implanted device, while using the same design equations commonly used in free-space.

Thus, the antenna resistance is preferably about the resistance of free space, approximately 377 Ohms, in order to provide better transmission. Alternatively, the resistance can be lower with the corresponding reduced transmission range. For example, for applications where a short transmission range is acceptable, a 50 ohm antenna can be used. These types of antennas are mass-produced and therefore readily available and lower cost than higher-resistance antennas.

In an example embodiment, the antenna range is less than 10 meters. This short range permits denser use of the devices, optimizing laboratory or clinic space.

Additionally, the use of a custom high impedance antenna matched to free-space or the higher output impedance of the VCO, eliminates the need for a power amplifier in the headstage output, allowing the VCO to drive the antenna directly. This novel usage results in a substantial power savings and reduction in overall system complexity.

The reduced power requirements permit use of between about 3.0 to about 3.6 volt battery, regulated by a fixed 2.8 volt supply with a 1.4 volt AC ground reference. This allows operating the entire device from a single battery (not shown), which is preferable. The battery is preferably a rechargeable battery that provides a reduced size per battery capacity. For example, currently, a rechargeable lithium-ion battery provides the greatest capacity with smallest size. Also, the battery can be preferably recharged through inductive coupling.

Currently, at least about 8 hours are needed to perform a neurological experiment, although some researchers desire as much as 24 hours. Therefore, the battery capacity should be adequate to provide at least about 8 hours of experiment time, more preferably at least about 24 hours.

The design of the present invention provides for a greatly reduced power consumption and reduced signal pathway. It does so primarily by using a low-power preamp, passive high-pass filtering, current-starved clock generators, low-power MUX buffer, high impedance MUX load, and a matched antenna driven directly by the VCO with no power amplifier. In a preferred embodiment, power consumption is about 4 mA at 2.8 V. This allows for greater than 24 hours of continuous operation from a miniature 100 mA-hr Li-Ion battery.

The power signal pathway is reduced because the signal from the MUX goes to the Voltage Control Oscillator (VCO) and the VCO output signal goes directly to the antenna. No power amplifier is needed prior to sending the signal to the antenna.

Figure 5:
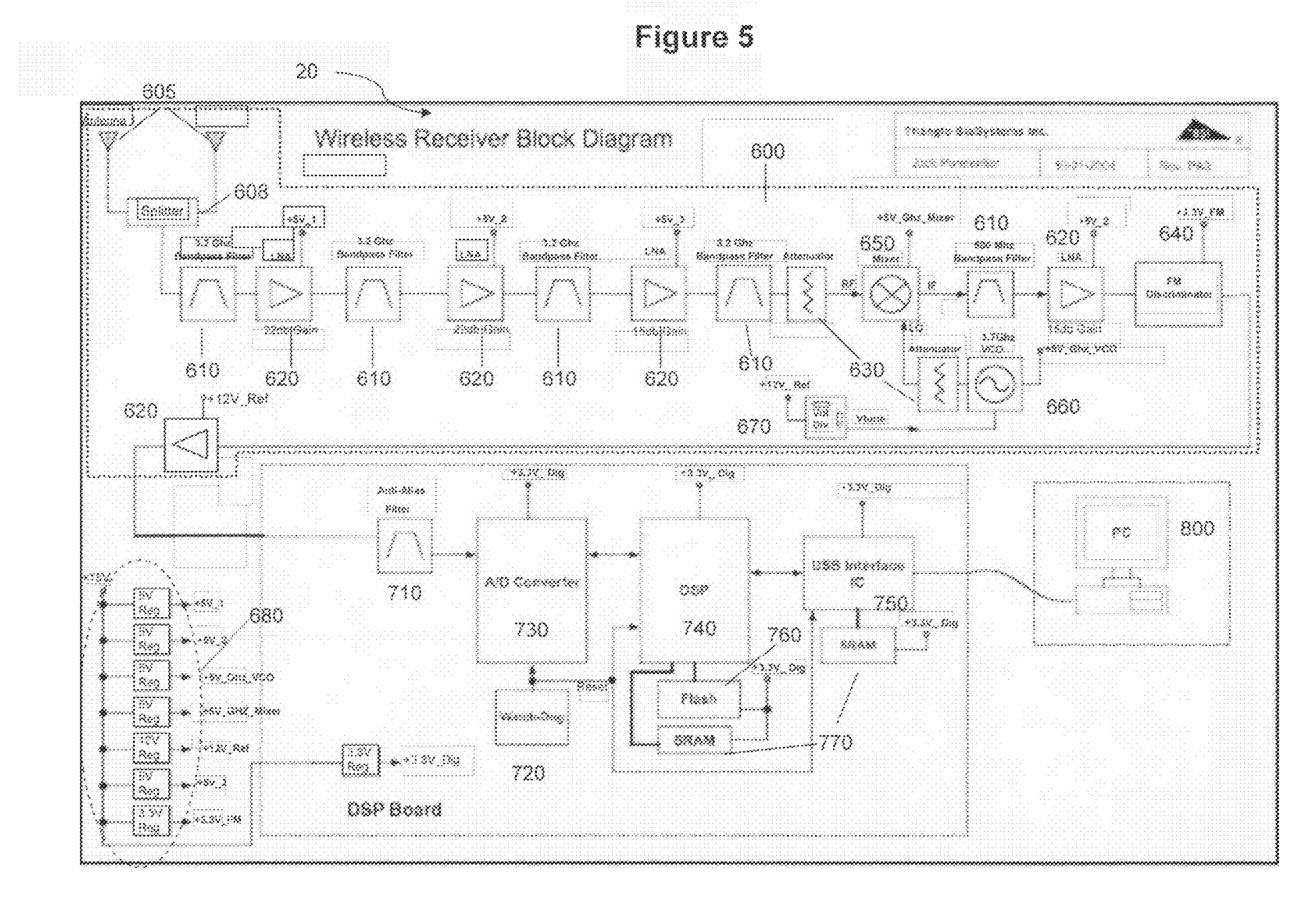
FIG. 5 is a schematic diagram of a receiver according to the present invention.

The wireless receiver, generally described as 20 in FIGS. 1 and 5, includes an RF receiver 600 and A/D converter and DSP 700.

The RF receiver 600 includes at least one antenna, a RF splitter, RF bandpass filters, RF amplifiers, RF attenuators, and an FM demodulator.

The RF receiver preferably uses antenna diversity to increase reliability. Multiple antennas 605 are preferably used to provide multiple signals that are then combined into a single signal at a splitter 608. Combining the signals allow for greater system reliability and signal strength by avoiding multipath interference. Multipath interference occurs when two or more incoming signals from the same source arrive at their destination along different paths. This interference is called destructive when the phase of the incoming signals is such that they cancel out at the receiver. Integrated antenna diversity systems reduce the probability of destructive interference at the receiver as a result of incoming multipath waves. Antenna diversity systems are those in which two or more antennas differing in one or more ways are incorporated onto the same platform. The received signals from the multiple antennas may then be combined, minimizing the probability of data loss.

There are four principal ways in which antennas are commonly made to differ in diversity systems. The first and most commonly used is frequency, or spread spectrum diversity, where an antenna is made to transmit at more than one frequency. In the present invention, it is preferable to use spread spectrum diversity is used at the transmitter not to overcome multipath interference, but to allow more than one device to be used in the same area simultaneously.

Another very common diversity technique consists in combining antennas of differing polarizations. Typically, though not necessarily, an antenna operate using two different orthogonal polarizations. A third technique, spatial diversity, is one in which the antennas are separated by some optimum distance. This distance is determined by a variety of factors including the wavelength of incoming signals and the anticipated angle of signal arrival. The fourth and final technique, pattern diversity, is one in which multiple antennas of differing patterns are used. In this final form of antenna diversity each pattern will fill in the "blind spots" or nulls of the other patterns. A null is that part of the three-dimensional space which the antenna cannot detect.

Spatial, polarization and pattern diversity schemes have been successfully used both together and individually to optimize our received signal reliability. Specifically we rotate one antenna 45 degrees with respect to the other to provide some measure of polarization diversity and space them a non-integer number of wavelengths apart to provide spatial diversity which is then optimized experimentally.

A combination of RF bandpass filters, RF amplifiers, and RF attenuators are used to filter, amplify and reduce reflected signal amplitudes respectively prior to demodulation. The RF bandpass filters 610 are necessary to filter out out-of-band signals like WiFi and Bluetooth, as well as unintentional radiators like microwave ovens. The amplifiers 620 boost the signal strength of the received signal. The RF attenuators 630 decrease the signal strength of both the forward and reflected signals arising from slight impedance mismatches. This is carefully tuned to maximize the amplitude of the desirable forward signal while keeping the reflected signal amplitude below the point where it will distort the demodulated output.

The FM demodulator 640 uses FM Phase discrimination to convert the radio signal into an output voltage. The FM phase discriminator uses the product of the received signal with a phase-delayed version of the received signal, followed by a low-pass filter to convert the FM frequency to an output voltage. While discriminators have been around since the 1940's, their use in receiving low-power biological signal transmissions is novel. All of the advantages provided by the wideband VCO are moot without an adequate low-noise receiver to track the frequency changes. Conventional FM receiver technology today uses Phase Locked-Loops (PLLs), but these are incapable of locking onto signal bands as wide as used in the present invention.

The RF receiver also includes a mixer 650 and a VCO 660 to down-convert the received signal to a more manageable frequency, relaxing the requirements on subsequent components in the signal path, which in turn increases the number of off-the-shelf components which meet our specifications. The VCO frequency is adjusted by an on-board resistor divider 670. The power supplies for each of the components in the receiver are generated 680 from a single regulated battery voltage to provide high stability and reliability in the signal quality.

The voltage output of the FM discriminator is band-pass filtered 710 to remove any high-frequency components which would alias into the signal bandwidth during analog to digital conversion. This signal, which matches the output of the MUX in our headstage, is then convert into a digital signal by the A/D converter 730. The Digital Signal Processor (DSP) 740 then interprets the TDM signal to extract a single digital sample from each block of time at which the analog MUX originally sampled an individual preamp output. This is done for each channel using real-time algorithms stored in Flash memory 760. Simultaneously, the digital signals are amplified and filtered to restore a high-fidelity reproduction of the original neural signal seen by the electrodes which is then stored in on-board SRAM memory 770. The amplification and filtering parameters can be modified by the user in real time.

The final task of the DSP is to output the data to a user-specified device. Two options exist. The data can be sent out a digital communication interface 750, such as a Universal Serial Bus (USB) port, to any PC 800 so equipped and then be displayed or recorded using any number of readily available software packages. The use of the USB eliminates the need for one of the very expensive commercially available data-acquisition systems available for biological signals. Alternatively the DSP can re-convert the digital stream into however many analog channels that are present in the headstage and output those in parallel to an oscilloscope or other data acquisition system (not shown). The ability to perform all of these functions in real time is a novel feature and a result of the careful component choice for the DSP that makes the receiver system very useful for biological applications.

The present invention achieves system robustness through the use of antenna pattern, polarization, and spatial diversity to improve reception, and frequency diversity to increase the number of simultaneous devices.

The present invention reduces power consumption through a variety of technical innovations—dual-subthreshold input MOSFETs require no power; the remainder of the input pre-amp uses less than 50 µW per channel; the MUX architecture is optimized for low-voltage operation; the RF Modulator is designed to drive an antenna without the need for a power-amplifier; the antennas are designed to radiate efficiently with low power, maximizing needed reliability at the expense of unnecessary range. Additionally, the low-range transmission permits multiple experiments or clinical neural data acquisition to be performed simultaneously in the same laboratory or clinic. The low-power consumption permits more channels/power source and/or more time/battery capacity.

The Wideband FM technology permits greater resolution of low-amplitude biological signals, higher phase noise tolerance with lower added noise, and large number of multiplexed analog channels to operate simultaneously.

Thus the low-range transmission in combination with the wideband FM technology permits multiple experimental or clinical applications to occur in closer proximity than prior art wireless technologies.

Importantly, robust chip design is used with the present invention because chip manufacturing tolerances in a typical CMOS process can vary by +/−50% of specified target. Also, because invasive neurological sampling is very sensitive and delicate surgery, minimum adjustment of the inserted electrodes is desirable. The present invention is thus designed with several key off-chip nodes at which the on-chip operating parameters can be tuned and optimized. Dual sub-threshold input MOSFETs allows for easy tuning of input high-pass filter cutoff frequencies. Digital on-chip memory and scan-chain allows real-time programming of individual channel gain as well as the ability to turn off inactive channels to save power and maximize operating time.

The present invention is also applicable for use in a method of neural data monitoring, including the steps of: (1) providing a wireless neural data acquisition system, as described above; and (2) acquiring data from the wireless neural data acquisition system. Furthermore, the present invention is applicable for use in a method of neural data monitoring, including the steps of: (1) implanting the headstage in a living being; (2) wirelessly transmitting data from the headstage; (3) receiving the data via the RF receiver; and (4) storing the data.

Certain modifications and improvements will occur to those skilled in the art upon a reading of the foregoing description. By way of example, one application for using the system and/or device of the present invention is in a method to monitor and/or control a prosthetic device by providing stimulation from a wireless neural system. Also, By way of example, one application for using the system and/or device of the present invention is in a method to therapeutically monitor and/or treat a living being by providing stimulation from a wireless neural system. All modifications and improvements have been deleted herein for the sake of conciseness and readability but are properly within the scope of the following claims.

What is claimed is:

1. A Wireless Neural Data Acquisition System, comprising:
   a headstage, an RF receiver, an analog-to-digital converter, a digital signal processor, and a communication interface,
   wherein the headstage comprises
      at least one Input Pre-amplifier high-pass filter,
      a multiplexer (MUX)
      an RF Modulator comprising a voltage control oscillator (VCO), and
      a transmitting antenna,
   wherein the Pre-amplifier is an on chip capacitor coupled high-pass filter where the output bias voltage and high-pass filter cutoff is tuned by adjusting the gate voltage of dual stacked on-chip sub-threshold MOSFETs for each channel with two off-chip tuning resistors for all channels, and the input impedance of the RF Modulator is such that it allows the MUX to drive the RF stage directly.

2. The system of claim 1, wherein the Pre-amplifier high-pass filter filters at 0.1-10 kHz bandwidth.

3. The system of claim 1, wherein the Pre-amplifier has user-selectable gain for all channels and for each channel individually.

4. The system of claim 1, wherein the MUX can multiplex at least 16 channels.

5. The system of claim 1, wherein the MUX multiplexes at least 32 channels.

6. The system of claim 1, wherein the MUX multiplexes at least 100 channels.

7. The system of claim 1, wherein the MUX multiplexes at least 250 channels.

8. The system of claim 1, wherein the MUX samples at greater than 50 kHz per channel.

9. The system of claim 1, wherein the transmitting antenna is a microstrip patch antenna.

10. The system of claim 9, wherein the transmitting antenna is a rectangular patch.

11. The system of claim 9, wherein the transmitting antenna is a planar inverted-f antenna.

12. The system of claim 1, wherein the transmitting antenna range is less than 10 meters thereby permitting denser use and circumventing FCC regulations.

13. The system of claim 1, wherein the RF receiver includes a receiving antenna wherein the impedance of the receiving antenna matches the impedance of the coaxial lines and the impedance of the transmission antenna matches the impedance of free-space and/or the output impedance of the VCO.

14. The system of claim 13, wherein the receiving impedance of the transmission antenna is 50 ohms and the transmission impedance is 377 ohms.

15. The system of claim 13, wherein the receiving antenna is multiple antennas and the system further includes an inverted splitter to combine multiple received signals.

16. The system of claim 15, wherein the multiple receiving antennas provide antenna diversity reception selected from the groups consisting of spatial, polarization, and pattern diversity.

17. The system of claim 15, wherein the multiple receiving antennas are microstrip patch antennas are configured for antenna diversity reception.

18. The system of claim 1, wherein the high-frequency wireless transmission range is about 2.5 GHz to about 4 GHz.

19. The system of claim 18, wherein the center frequency is selected from the group consisting of about 2.8, about 3.2, and about 3.6 GHz.

20. The system of claim 1, wherein the FM modulator uses wideband frequency modulation of about 10% of the center frequency.

21. The system of claim 20, wherein the wideband frequency modulation is about 300 MHz.

22. The system according to claim 1, wherein the communication interface is a USB interface.

23. The system according to claim 1, wherein the communication interface is an analog interface.

24. The system according to claim 1, further including a power supply.

25. The system according to claim 24, wherein the power supply is a lithium ion rechargeable battery or a 3.0-3.6 Volt battery regulated to a fixed 2.8 volt supply with 1.4 volt AC ground reference.

26. The system according to claim 24, where the power supply includes a battery with inductive coupling to recharge the battery.

27. The system according to claim 1, further including a microprocessor with software for capturing the data.

28. The system according to claim 1, wherein the headstage is designed and packaged to record and transmit when implanted subcutaneously.

29. The system according to claim 1, where the transmitting antenna is designed to transmit through tissue when implanted.

30. The system of claim 1, wherein:
   the headstage comprises:
      at least one Input Pre-amplifier high-pass filter and amplifier,
      an input control,
      a multiplexer (MUX),
      an RF Modulator comprising a voltage control oscillator (VCO),
      a transmitting antenna,
      and a power supply;
   the RF receiver comprises:
      at least one receiving antenna,
      at least one RF bandpass filter,
      at least one RF amplifier,
      at least one RF attenuator, and
      an FM Demodulator;
   wherein the pre-amplifier is an on chip capacitor coupled high-pass filter where the output bias voltage and high-pass filter cutoff is tuned by adjusting the gate voltage of dual stacked on-chip sub-threshold MOSFETs for each channel with two off-chip tuning resistors for all channels,
      the input impedance of the RF modulator is such that it allows the MUX to drive the RF stage directly,
      the antenna impedance is matched to the VCO output,
      the FM demodulator is an FM phase discriminator, and
      the A/D converter and DSP provide real-time signal processing;
   wherein the components are connected such that the input signal coming from the electrode goes through an ac coupled high-pass filter then to the amplifier then to the MUX and combine in a single time sequence then to the RF modulator then to the transmitting antenna then to the RF receiver antenna(s) then to at least one RF bandpass filter, RF amplifier, and RF attenuator then to the FM demodulator then to the communication interface; thereby providing increased power efficiency, compact headstage size, robust wireless signaling and multiplexing for accurate, reliable transmission of neural signal data.

31. A wireless neural data acquisition headstage, comprising:
   at least one Input Pre-amplifier high-pass filter and amplifier,
   a multiplexer (MUX),
   a clock, and
   an RF Modulator comprising:
      a voltage control oscillator (VCO),
      a transmitting antenna, and
      a power supply;
   wherein the pre-amplifier is an on chip capacitor coupled high-pass filter where the output bias voltage and the filter cutoff is tuned by adjusted the gate voltage of dual stacked sub-threshold MOSFETs for each channel using two off-chip tuning resistors for all channels, the input impedance of the RF modulator is such that it allows the MUX to drive the RF stage directly, and the antenna impedance is matched to the VCO output; wherein the components are connected such that the input signal coming from an electrode goes through the high-pass filter then to the amplifier then to the MUX then to the RF modulator then to the transmitting antenna; thereby providing increased power efficiency, compact headstage size, robust wireless signaling and multiplexing for accurate, reliable transmission of neural signal data.

32. The system of claim 31, wherein the Pre-amplifier high-pass filter filters at 0.1-10 kHz bandwidth.

33. The system of claim 31, wherein the input amplifier has user-selectable gain for all channels and for each channel individually.

34. The system of claim 31, wherein the MUX can multiplex at least 16 Channels.

35. The system of claim 31, wherein the MUX multiplexes at least 32 channels.

36. The system of claim 31, wherein the MUX multiplexes at least 100 channels.

37. The system of claim 31, wherein the MUX multiplexes at least 250 channels.

38. The system of claim 31, wherein the MUX samples at greater than 50 kHz per channel.

39. The system of claim 31, wherein the transmitting antenna is a microstrip patch antenna.

40. The system of claim 39, wherein the transmitting antenna is a rectangular patch.

41. The system of claim 39, wherein the transmitting antenna is a planar inverted-f antenna.

42. The system of claim 31, wherein the transmitting antenna range is less than 10 meters.

43. The system of claim 31, wherein the impedance of a receiving antenna matches the impedance of the coaxial lines and the impedance of the transmission antenna matches the impedance of free-space and/or the output impedance of the VCO.

44. The system of claim 43, wherein the receiving impedance of the transmitting antenna is 50 ohms and the transmission impedance is 377 ohms.

45. The system of claim 31, wherein the high-frequency wireless transmission range is about 2.5 GHz to no greater than about 4 GHz.

46. The system of claim 45, wherein the center frequency is selected from the group consisting of about 2.8, about 3.2, and about 3.6 GHz.

47. The system of claim 31, wherein the FM modulator uses wideband frequency modulation of about 10% of the center frequency.

48. The system of claim 47, wherein the wideband frequency modulation is about 300 MHz.

49. The system according to claim 31, wherein the power supply is a 3.0-3.6 Volt battery regulated to a fixed 2.8 volt supply with 1.4 volt AC ground reference.

50. The system according to claim 31, wherein the power supply is a lithium ion rechargeable battery.

51. The system according to claim 31, where the power supply battery includes inductive coupling to recharge the battery.

52. The system according to claim 31 where the transmitting antenna is designed to transmit through tissue when implanted.

53. The system according to claim 31 where the headstage is designed and packaged to record and transmit when implanted subcutaneously.

54. A method of neural data monitoring, comprising the steps of:
   providing a wireless neural data acquisition system, having a headstage, an RF receiver, an analog-to-digital converter, a digital signal processor, and a communication interface,
   wherein the headstage comprises
      at least one Input Pre-amplifier high-pass filter,
      a multiplexer (MUX)
      an RF Modulator comprising a voltage control oscillator (VCO), and
      a transmitting antenna,
   wherein the Pre-amplifier is an on chip capacitor coupled high-pass filter where the output bias voltage and high-pass filter cutoff is tuned by adjusting the gate voltage of dual stacked on-chip sub-threshold MOSFETs for each channel with two off-chip tuning resistors for all channels, and the input impedance of the RF Modulator is such that it allows the MUX to drive the RF stage directly, and
   acquiring data from the wireless neural data acquisition system.

55. The method of claim 54, further comprising the steps of:
   implanting the headstage in a living being;
   wirelessly transmitting data from the headstage;
   receiving the data via the RF receiver; and
   storing the data.

* * * * *

UNITED STATES PATENT AND TRADEMARK OFFICE
CERTIFICATE OF CORRECTION

PATENT NO.         : 7,346,312 B2
APPLICATION NO. : 10/971915
DATED               : March 18, 2008
INVENTOR(S)       : Irazoqui-Pastor et al.

It is certified that error appears in the above-identified patent and that said Letters Patent is hereby corrected as shown below:

The title page showing the illustrative figure should be deleted to be replaced with the attached title page.

The drawing sheets, consisting of Figs. 1 and 5, should be deleted to be replaced with the drawing sheets, consisting of Figs. 1 and 5, as shown on the attached page.

In Column 11, Line 63, the word "are" should be deleted after the word antennas.

Signed and Sealed this

First Day of July, 2008

JON W. DUDAS
*Director of the United States Patent and Trademark Office*

United States Patent
Irazoqui-Pastor et al.

(10) Patent No.: US 7,346,312 B2
(45) Date of Patent: Mar. 18, 2008

(54) WIRELESS NEURAL DATA ACQUISITION SYSTEM

(75) Inventors: Pedro Irazoqui-Pastor, Durham, NC (US); James C Morizio, Durham, NC (US); Vinson L. Go, Wake Forest, NC (US); Jack D Parmentier, Apex, NC (US)

(73) Assignee: Triangle BioSystems, Inc., Durham, NC (US)

( * ) Notice: Subject to any disclaimer, the term of this patent is extended or adjusted under 35 U.S.C. 154(b) by 320 days.

(21) Appl. No.: 10/971,915

(22) Filed: Oct. 23, 2004

(65) Prior Publication Data

US 2006/0089112 A1    Apr. 27, 2006

(51) Int. Cl.
*H04B 1/04* (2006.01)
*A61B 5/04* (2006.01)

(52) U.S. Cl. ............... 455/41.2; 455/334; 455/349; 600/546; 600/373

(58) Field of Classification Search ........... 455/232.1, 455/296, 307, 311, 313, 334, 341, 344, 41.2, 455/42, 349; 600/546, 373, 300; 330/278, 330/295
See application file for complete search history.

(56) References Cited

U.S. PATENT DOCUMENTS 6,402,689 B1 * 6/2002 Scarantino et al. ......... 600/300
7,187,967 B2 * 3/2007 Kennedy ..................... 600/544
2005/0090756 A1 * 4/2005 Wolf et al. .................. 600/546

OTHER PUBLICATIONS

Pedram Mohseni, Khalil Najafi, "A Low Power Fully Integrated Bandpass Operational Amplifier for Biomedical Neural Recording Applications," 24th Annual International Conference of the IEEE Engineering in Medicine and Biology Society, Houston, TX (Oct. 23-26, 2002).
Pedro Irazoqui-Pastor, Istvan Mody, and Jack W. Judy, "In-Vivo EEG Recording Using a Wireless Implantable Neural Transceiver," 1st International IEEE EMBS Conference on Neural Engineering, Capri Island, Italy (Mar. 20-22, 2003).
Irazoqui-Pastor, Pedro. (2003) Transcutaneous Inductively Powered Neural Recording System [Doctoral Dissertation].University of California: Los Angeles (CA).

* cited by examiner

*Primary Examiner*—Blane J. Jackson
(74) *Attorney, Agent, or Firm*—MacCord Mason PLLC (57) ABSTRACT

A Wireless Neural Data Acquisition System for increased power efficiency, compact size, robust signaling and reliable transmission is shown and described. In one embodiment, the system includes a headstage, an RF receiver, an analog-to-digital converter, a digital signal processor, and a communication interface. The headstage includes at least one input pre-amplifier high-pass filter and amplifier, a multiplexer (MUX), an RF Modulator comprising a voltage control oscillator (VCO), a transmitting antenna, and a power supply. The RF receiver includes at least one receiving antenna, at least one bandpass filter, at least one amplifier, at least one attenuator, and an FM Demodulator.

55 Claims, 5 Drawing Sheets

Figure 1

Figure 5